(12) United States Patent
Desjardins-Lavisse et al.

(10) Patent No.: US 8,784,848 B2
(45) Date of Patent: Jul. 22, 2014

(54) METHOD FOR PREPARING A STABLE OIL-IN-WATER EMULSION

(75) Inventors: Isabelle Desjardins-Lavisse, Henrichemont (FR); Stéphane Desobry, Saint-Remimont (FR)

(73) Assignee: SAS Genialis, Henrichemont (FR)

( * ) Notice: Subject to any disclaimer, the term of this patent is extended or adjusted under 35 U.S.C. 154(b) by 0 days.

(21) Appl. No.: 13/379,652

(22) PCT Filed: Jun. 22, 2010

(86) PCT No.: PCT/EP2010/058848
§ 371 (c)(1),
(2), (4) Date: Mar. 16, 2012

(87) PCT Pub. No.: WO2010/149668
PCT Pub. Date: Dec. 29, 2010

(65) Prior Publication Data
US 2012/0183584 A1     Jul. 19, 2012

(30) Foreign Application Priority Data

Jun. 24, 2009 (FR) .................................... 09 54323

(51) Int. Cl.
| *A61K 9/107* | (2006.01) |
| *A61K 47/00* | (2006.01) |
| *A61P 17/00* | (2006.01) |
| *B01F 11/00* | (2006.01) |

(52) U.S. Cl.
USPC ............................ 424/400; 514/772; 366/116

(58) Field of Classification Search
USPC .................... 424/450, 489; 208/187; 426/601
See application file for complete search history.

(56) References Cited

U.S. PATENT DOCUMENTS 2,893,707 A * 7/1959 Gulton .......................... 366/118
6,465,015 B1 * 10/2002 Mohseni et al. .............. 424/489

FOREIGN PATENT DOCUMENTS

| DE | 10 2006 032 083 A1 | 1/2008 |
| EP | 0649867 | * 12/1993 |
| EP | 0 692 237 A1 | 1/1996 |
| FR | 1 322 103 A | 3/1963 |

OTHER PUBLICATIONS

Abismail, B, Emulsification by ultrasound: drop size distribution and stability, Ultrasonics Sonochemistry, 6, 1999, 75-83.*
Kentish et al., The use of ultrasonics for nanoemulsion preparation, ScienceDirect 9:170-5, 2008.
International Search Report for international application No. PCT/EP2010/058848.

* cited by examiner

*Primary Examiner* — Frederick Krass
*Assistant Examiner* — Celeste A Roney
(74) *Attorney, Agent, or Firm* — McDonnell Boehnen Hulbert & Berghoff LLP

(57) ABSTRACT

The invention relates to a method for preparing a stable oil-in-water emulsion without adding an emulsifier. According to the method, a mixture of a lipid phase and an aqueous phase is subjected to vibrating energy, in a sealed container, by applying a transducer operating at a frequency of more than 900 kHz.

18 Claims, 4 Drawing Sheets

METHOD FOR PREPARING A STABLE OIL-IN-WATER EMULSION

CROSS REFERENCE TO RELATED APPLICATIONS

This application is a 35 U.S.C. 371 National Application of PCT/EP2010/058848, filed Jun. 22, 2010, which claims priority to French Patent Application No. 09 54323, filed Jun. 24, 2009.

The present invention relates in general to the field of emulsions, and more particularly to a method of preparing a stable emulsion of a lipid phase in an aqueous phase which does not require the addition of an emulsifier.

As is known, an emulsion is a mixture of two immiscible liquid substances (which do not normally mix), such as water and oil. The liquid forming the drops is known as the internal, discontinuous or dispersed phase, while the liquid surrounding the droplets is known as the continuous or external phase. In an oil-in-water emulsion, the oil is dispersed in the water in the form of small droplets.

Whether the emulsion is an oil-in-water (O/W) or water-in-oil (W/O) emulsion, it is typically unstable and tends to separate or coalesce. An emulsifier is accordingly added to ensure that the mixture of the two immiscible phases remains stable.

The basic principle when it comes to obtaining an O/W emulsion therefore consists in general in finely dispersing the lipid phase in the water in the presence of an emulsifier.

This dispersion is in fact obtained by subjecting the mixture of the aqueous and lipid phases, with the emulsifier, to vigorous stirring with grinding, that is to say under severe shearing, which may typically be achieved by:
 a colloid mill;
 a high pressure emulsifier/homogeniser;
 an ultrasonic emulsifier.

Apart from the addition of emulsifier, another important factor for the stability of an emulsion is the size of the particles of the discontinuous phase: the smaller are these particles, the stabler is the emulsion over time.

Thus, a high pressure emulsifier/homogeniser is commonly used industrially because it allows very small particle sizes to be obtained, namely of the order of 200 nm (or even less). In such an apparatus, a plunger pump forces the mixture to be emulsified through an adjustable orifice. The smaller is the orifice, the higher is the indicated pressure. On passing through this obstacle the fluid is exposed to various stresses producing significant shearing which causes the formation of fine micelles or globules dispersed in the continuous phase. Today numerous industrial sectors use these apparatuses, which are capable of reaching 1,500 to 3,000 bar in continuous production, for instance the cosmetics industry, the pharmaceuticals industry and the foodstuffs industry (ingredients, beverages, etc.).

In the agri-food sector, the use of waves of ultrasonic frequencies was proposed for example for preparing nano-emulsions in an article entitled "The use of ultrasonics for nanoemulsion preparation" by S. Kentisch et al. (Innovative Food Science and Emerging Technologies 9 (2008) 170-175). The method described uses an ultrasonic transducer with a frequency of 20 to 24 kHz. The O/W emulsion obtained has an average droplet size of the order of 135 nm using a mixture of linseed oil and water, in the presence of a surfactant (Tween 40).

Other tests relating to the preparation of emulsions with synthetic products have been carried out in the field of paints or polymers. Overall, the methods for preparing emulsions by applying ultrasound (or "sonication") exploit the phenomenon of cavitation which allows rapid emulsification under severe shearing.

It has been stated that stability is an important aspect of emulsions, especially when they are transported and stored prior to use, two influential parameters in this respect being the size of the discontinuous phase and the emulsifier.

However, for certain applications it would be desirable to be able to dispense with an emulsifier. In the fields of dermatology and cosmetics for example, emulsions of the oil-in-water type are today highly valued for their convenience of use and their coolness. To avoid the need to use surfactants to stabilise this type of emulsion, since they may prove to irritate certain types of skin, EP 0 692 237 proposes the use of hollow expanded thermoplastic particles of acrylonitrile polymer or copolymer to disperse the oil phase.

Another field for which the possibility of preparing emulsions without conventional emulsifiers or stabilisers is of major interest is the agri-food sector. The elimination of emulsifiers makes it possible to simplify formulations and to overcome the problems of allergies or intolerance associated with this type of compound, which is particularly beneficial in the development of products for "nutrition/health" applications.

DE 10 2006 032 083 A1 describes a method of manufacturing microcapsules containing a lipophilic agent. The method involves the performance of multiple emulsification steps, including emulsification of an O/W emulsion in a lipid phase using ultrasound. The examples described are directed at ultrasonic frequencies of the order of 20 kHz to 40 kHz.

FR 1 322 103 relates to a method of producing O/W emulsions which consists of mixing the oily substance and the aqueous liquid together mechanically, emulsifying said mixture at a suitable temperature (for example 60° C.) by vibrations greater than or equal to 10 kHz, preferably between 15 and 30 kHz, then injecting said emulsion drop by drop in the appropriate direction into the focusing zone of a piezo-electric cup operating at between 800 kHz and 1 MHz.

The latter two methods are therefore complex, use ultrasonic treatment with cavitation, and require multiple operations involving the phases to be emulsified, in differing volumes.

OBJECT OF THE INVENTION

The object of the present invention is therefore to propose a method of preparing emulsions which are stable for several weeks to several months which does not require any emulsifier and which is simple to carry out.

GENERAL DESCRIPTION OF THE INVENTION

In accordance with the present invention, a method is proposed of preparing a stable O/W emulsion, in which a lipid (or lipophilic) phase is combined with an aqueous (or hydrophilic) phase, characterised in that the mixture of these phases is exposed to vibratory energy, in a closed receptacle, by application of a transducer operating at a frequency greater than or equal to 900 kHz, preferably greater than 1 MHz.

This high-frequency vibratory treatment may typically be continued until the desired final lipid phase concentration and/or the final desired particle size is obtained, or more simply until complete dispersion of the lipid phase, after which the emulsion may be removed.

During its development, the process surprisingly revealed that it is possible to produce a stable oil-in-water emulsion without the addition of an emulsifier, by exposing the mixture to waves generated by application of a transducer operating at a frequency greater than or equal to 900 kHz. The transducer preferably operates within a frequency range defined by a lower limit of the order of 900 KHz to 1 MHz and by an upper limit of the order of 3 MHz. A narrower range may extend up to 1.5 MHz.

The method according to the invention allows the obtainment of stable emulsions with a fine and controlled particle size, the particles of the discontinuous phase being of a micrometric or nanometric size. These emulsions may be stable for up to several months, and are therefore suitable for industrial use. They are, moreover, immediately and infinitely soluble in any other aqueous medium.

Preferably, the vibratory treatment using the transducer is carried out until a micrometric particle size is obtained for the discontinuous phase. It is in particular intended to achieve an average particle (globule) diameter of the discontinuous phase which is less than 50 µm, more preferably less than 20 µm. Conventionally, in the context of a Gaussian distribution, the average diameter corresponds to the average of the diameters of the fatty globules measured by volume in the emulsion.

Without wishing to be limited by a theoretical explanation, it is thought that the application of high frequency vibratory energy (900 kHz or more) by means of a transducer to produce emulsions has the advantage of eliminating the cavitation phenomenon generally used due its shearing intensity. This is because the frequency ranges conventionally used of between 20 and 200 kHz, and generally lower than 80 kHz, result in formation of cavitation bubbles in which the local temperature increases up to several hundreds of degrees Celsius and where the pressure increases very greatly. This cavitation causes severe shearing of the mixture, which allows rapid emulsification but causes physico-chemical and biochemical degradation of the mixture. The use of high frequencies in accordance with the present invention eliminates this degradation and preserves the product much better, allowing stable emulsions to be obtained. The present method is in particular thought to be based on a phenomenon of closed vessel misting which leads to re-solubilisation of the micro/nano droplets formed at the surface (caused by the high-frequency waves of the transducer, preferably of the piezoelectric type) and progressive emulsification of the mixture. These fatty globules may have micrometric (or even nanometric) dimensions as a function of the time for which the method is applied.

Another phenomenon implemented in the invention is slight acidification of the emulsion obtained, which would appear to indicate partial ionisation of the emulsion. Since such ionisation arises through the interplay of electrostatic bonds; this makes it possible to further reinforce the stability of the emulsion and to dispense with an emulsifier in the formulation.

Thus, compared with (low frequency) ultrasonic emulsification by cavitation which takes place under very severe shearing with the associated drawbacks, the present method is a direct emulsification method which allows a stable, fine emulsion to be obtained. While emulsification takes longer (typically one to several hours) than in the cavitation methods, the present method has the advantage of guaranteeing product integrity.

The present method is suitable for general application in all industrial sectors, and is of particular interest where emulsifiers may pose problems of convenience, irritation, allergies or intolerance such as, for example in the agri-food, dermatological and cosmetics sectors, relaxation products and pharmacy. Other sectors of interest are for example paints or polymers.

Of course, the elimination of emulsifiers makes it possible to reduce costs, and is thus attractive for all industrial scale emulsion preparations.

It will be understood that the composition of the phases will typically depend on the sector in question. The formulation of the mixture to be emulsified may additionally comprise one or more additives. Since the addition of emulsifier is possible but not required, it will preferably be avoided. The two phases formulated may simply be combined in the processing receptacle, but may also be pre-mixed.

In general, the term lipid (or lipophilic) phase denotes any oily substances which are liquid at the temperature at which the method is carried out and which may be of natural, vegetable or animal origin, or of synthetic origin, with or without proven biological activity, and insoluble in water (less than 2% by weight at ambient temperature). The following may in particular be listed by way of non-limiting examples of these lipids:
  for agri-food: vegetable oils (olive, sunflower, rapeseed, peanut, mixtures of vegetable oils etc.); animal oils (fish etc.), butters etc.
  for dermatology/cosmetics: avocado, argan and other vegetable oils, essential oils.

The term aqueous (or hydrophilic) phase denotes all phases containing water and/or alcohol. Water, softened or unsoftened, mineral or non-mineral or spring water may be mentioned.

Furthermore, the mixture to be emulsified may comprise additives. These additives may be added to one of the phases, depending on whether they are fat-soluble or water-soluble. If applicable, such an additive may be previously solubilised in a solvent. By way of non-exhaustive example, in the food sector biomolecules of interest could be added to the aqueous phase (peptides, vitamins, flavonoids etc.) or to the lipid phase (triacylglycerols, fatty acids, fragrances etc.).

In practice, the mixture to be emulsified is placed in a receptacle which is kept closed during application of the high-frequency waves. These waves are preferably applied to the mixture in the bottom part of the receptacle.

Transducers of the piezoelectric type are particularly preferred; they are suited to stable operation in the selected frequency range and their manufacturing technology is well understood. Furthermore, ceramic piezoelectric elements may be directly in contact with, or immersed in, the medium to be treated. Alternatively, the transducer may comprise a mechanically vibrating element coupled to piezoelectric ceramic elements, this then being brought into contact with, or immersed in, the medium to be treated.

The vibrations are applied preferably for the time needed to disperse the lipid phase fully and to achieve the desired particle size distribution. The required periods may be easily estimated by a person skilled in the art on the basis of prior tests, taking account of the phases present, of volumes, and of the applied power.

It will be noted that it is possible to use a plurality of transducers at the same time to produce one and the same emulsion, which makes it possible in particular to reduce the time needed for emulsification.

For good control of the method, the proportion of lipid phase is preferably of the order of 0.01 to 40% of the total weight of the mixture (emulsion), more preferably the proportion of lipid phase does not exceed 30% (wt./wt.) of the total weight, or better does not exceed 20% (wt./wt.).

In some cases, depending on the treatment period, an increase in mixture temperature may be observed, caused by continuous operation of the transducers. To overcome such an increase in temperature, the mixture will preferably be kept within a predetermined temperature range, preferably within a temperature range of between 20 and 30° C. This is easily achieved by providing the closed receptacle with cooled double wall, or by any other suitable means. Such cooling is particularly useful if the mixture to be emulsified contains heat-sensitive or volatile products, such as certain essential oil fragrances, for example.

According to another aspect of the invention, a stable W/O emulsion, with no emulsifier, is proposed, with a micrometric or nanometric particle size. This emulsion remains stable over several weeks, typically at least 3 months, at ambient temperature. Such an emulsion is advantageously obtained by the present method. Yet another aspect of the invention relates to a composition or product for pharmaceutical, dermatological or food use comprising an emulsion obtained according to the present method.

According to yet another aspect of the invention, use of the present method is proposed for preparing dermatological or pharmaceutical compositions or food products.

According to a final aspect, the present invention relates to an emulsifying device comprising a closed receptacle suitable for receiving a lipid phase and aqueous phase mixture to be emulsified. A transducer is arranged so as to apply vibrations to the mixture in the lower part of the closed receptacle, the transducer being configured and driven by control electronics suitable for operating in a frequency range of between 900 kHz and 3 MHz.

The device preferably comprises means for keeping the mixture in said closed receptacle at a temperature within a predetermined temperature range, preferably in a temperature range of between 20 and 30° C.

DETAILED DESCRIPTION WITH REFERENCE TO THE FIGURES

Other distinctive features and characteristics of the invention will be revealed by the detailed description of some advantageous embodiments given below by way of example, with reference to the appended drawings, in which.

Figure 1:
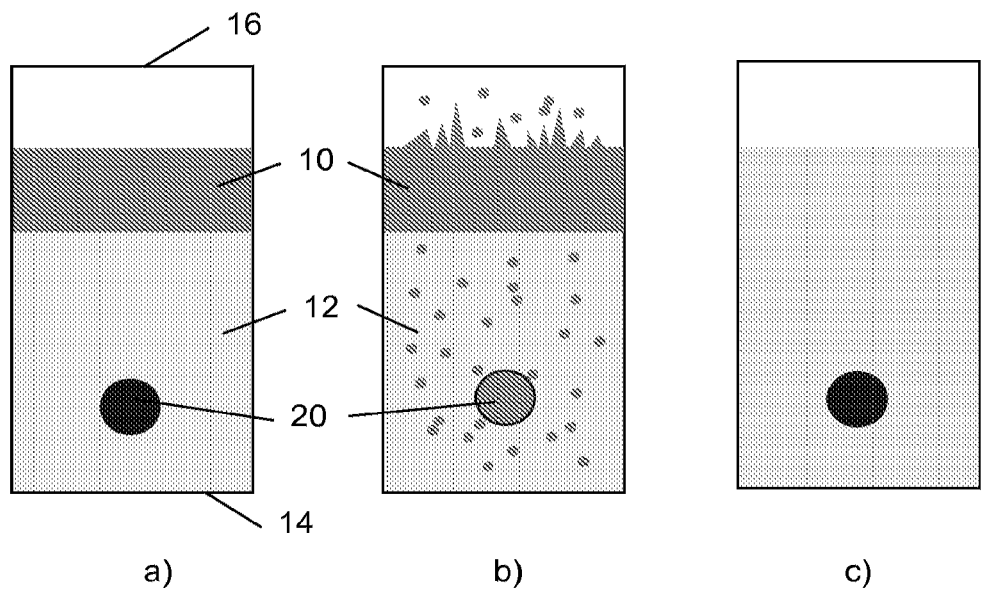
FIG. 1 is a diagram illustrating the principle of emulsification used in the present method in three steps: a) initial state, b) transducer in operation, and c) final state.

The principle of the present method is shown schematically in FIG. 1. A biphase mixture comprising a lipid phase 10 and an aqueous phase 12 is prepared and placed in a receptacle 14. In the configuration of FIG. 1 a), the aqueous phase 12 was poured in first, then the lipid phase 10. The receptacle 14 is then closed by a cover 16. Reference sign 20 indicates a piezoelectric transducer operating at a frequency greater than 900 kHz, applied after closure of the receptacle 14. This piezoelectric transducer 20 allows vibratory energy to be applied to the mixture substantially without cavitation, which results in the formation of fine droplets at the surface (misting), which, when they fall back down into the solution, result in the progressive formation of a very fine, stable and homogeneous emulsion. This is because an emulsion of micrometric (or even nanometric) size is obtained by operating the transducer for a period varying from several minutes to several hours, depending on the phases and volumes in question. Vibratory treatment is interrupted after obtainment of the final desired lipid phase concentration and/or the final desired particle size, or more simply once the lipid phase is completely dispersed, after which the emulsion may be removed. Preferably, the vibratory treatment is stopped once the final desired particle size distribution is obtained.

It will be noted that the piezoelectric transducer 20 is immersed in the mixture to be treated, at the bottom of the receptacle 14, and preferably at the centre (viewed in horizontal section) of the receptacle. It may be situated in the lower half of the volume to be treated, and preferably in the first third. In the present variant, the ceramic piezoelectric elements are directly in contact with the mixture to be treated. While just one transducer 20 is shown in FIG. 1, a plurality of transducers could also be used operating at the prescribed frequencies and distributed over the receptacle, so reducing the treatment period.

Application of the present method to a single biphase "oil+water" mixture, without emulsifier, has demonstrated that the process does not in any way degrade the oil used (the degree of unsaturation of the fatty acid chains is preserved) and that the emulsion is stable for several months at ambient temperature. Moreover, the emulsion obtained perfectly withstands the processes of sterilisation and pasteurisation.

It will additionally be noted that in the present method, as illustrated in FIG. 1, the two phases to be treated are typically combined in the receptacle 14 in the desired proportions for the emulsion to be obtained. The vibratory treatment is therefore applied to a combined volume of aqueous and lipid phases, the respective proportions of which are those of the desired emulsion. Thus, a sufficient volume of lipid phase is placed from the start in the receptacle to achieve the desired concentration of dispersed phase for the emulsion to be produced.

Figure 8:
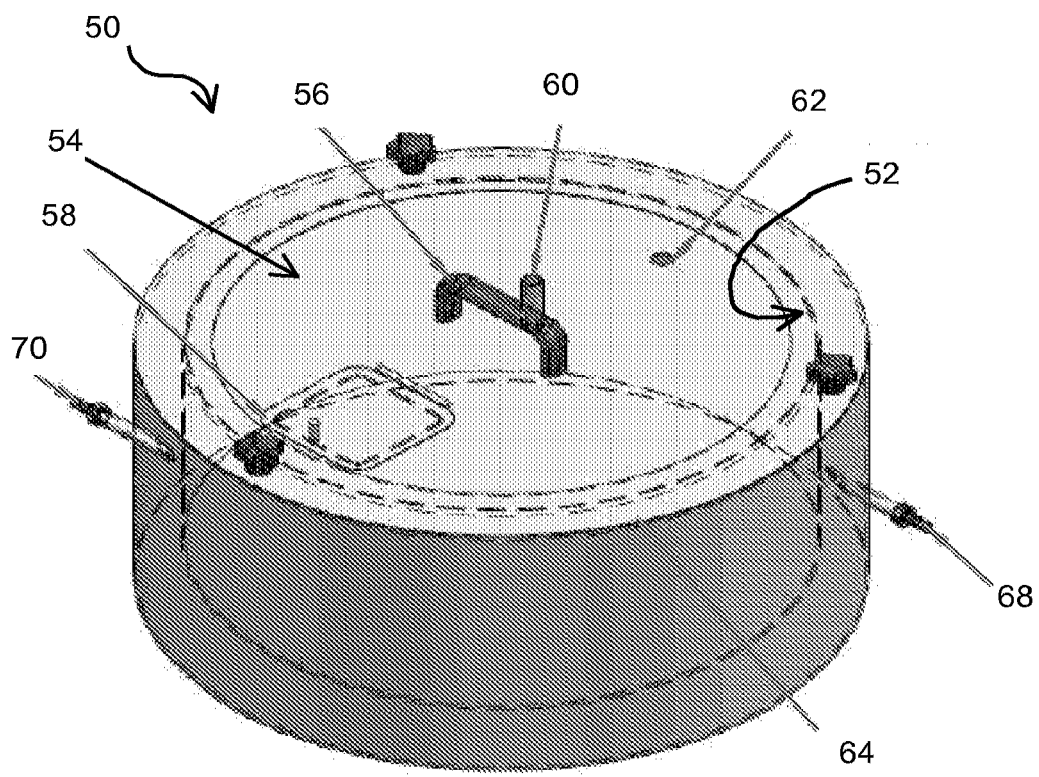
FIG. 8 is a perspective view of a variant tank for carrying out the present method.

While in the embodiment described above the aqueous phase 12 is poured in first followed by the lipid phase 10, it would be possible to produce a premix in the same proportions, for example by stirring, before pouring this premix into the receptacle 14. FIG. 8 shows an embodiment of the tank 50 for carrying out the present method. It comprises an inner tank 52 defining a volume intended to receive the mixture to be emulsified and closed by a cover 54. The cover 54 is equipped with a handle 56 and comprises an inspection hatch 58, a wire duct 60 and a measurement orifice 62. One or more transducers operating at the prescribed frequencies (not shown) are fitted in the lower part of the tank 52.

Reference sign 64 indicates an outer wall, concentric with the inner wall of the tank 52, which therefore defines an annular space 66 for a cooling fluid. The nozzles 68 and 70 will therefore be used respectively as inlet and outlet for a cooling fluid such as water or another suitable fluid. This jacketed or double-walled configuration of the treatment tank makes it straightforwardly possible to keep the mixture in the tank within a predetermined temperature range, preferably from 20 to 30° C. The flow rate and temperature of the cooling fluid will therefore be regulated accordingly.

Example 1

An emulsion was produced using the present method under the operating conditions illustrated in FIG. 1 and starting from a 500 mL mixture comprising Evian water and 5% (percentage by weight) of Inca Inchi oil, relative to the total weight of the mixture (without emulsifier). The method is carried out in a room at 20° C., and the piezoelectric transducer was energised for 10 hours.

Figure 2:
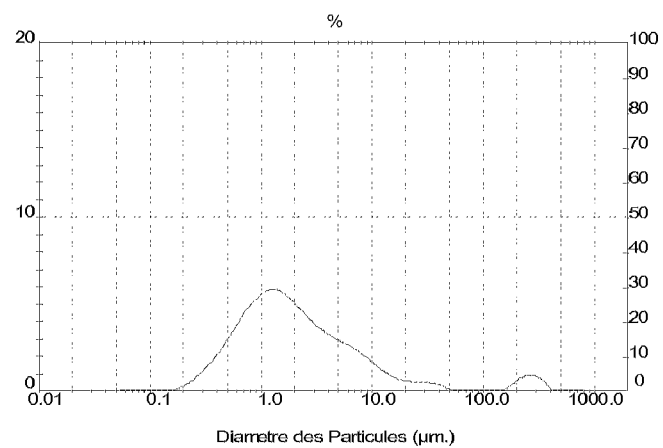
FIG. 2 is a graph showing the size distribution of the lipid phase according to Example 1.

The size distribution of the fatty globules in the emulsion obtained is shown in the graph of FIG. 2. The emulsion is fine and is on a micrometric scale, with an average diameter of 1.75 μm.

The emulsion is stable for several weeks at ambient temperature.

A centrifugation test for 20 minutes at 4000 rpm with an acceleration of 3500 g has not caused any phase change. The emulsion may therefore be considered stable.

Comparative Example 1

An emulsion was prepared with the same water/Inca Inchi mixture as in Example 1 above with the aid of 5 cycles of a high-pressure 1700 bar "Emulsiflex" emulsifier-homogeniser at 20° C.

Figure 3:
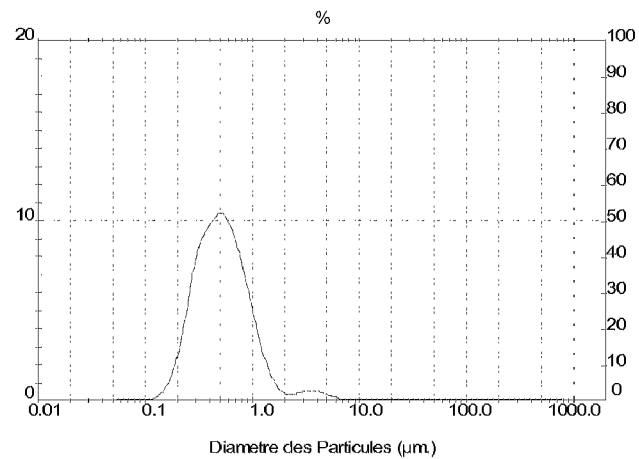
FIG. 3 is a graph showing the size distribution of the lipid phase according to comparative example 1.
Figure 4:
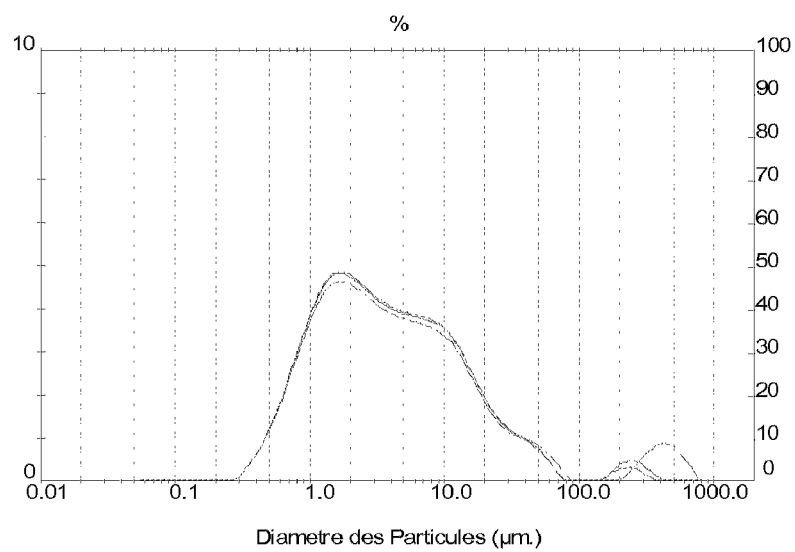
FIGS. 4 to 7 are graphs showing the size distribution of the lipid phase for the other emulsions numbered 2 to 5.
Figure 5:
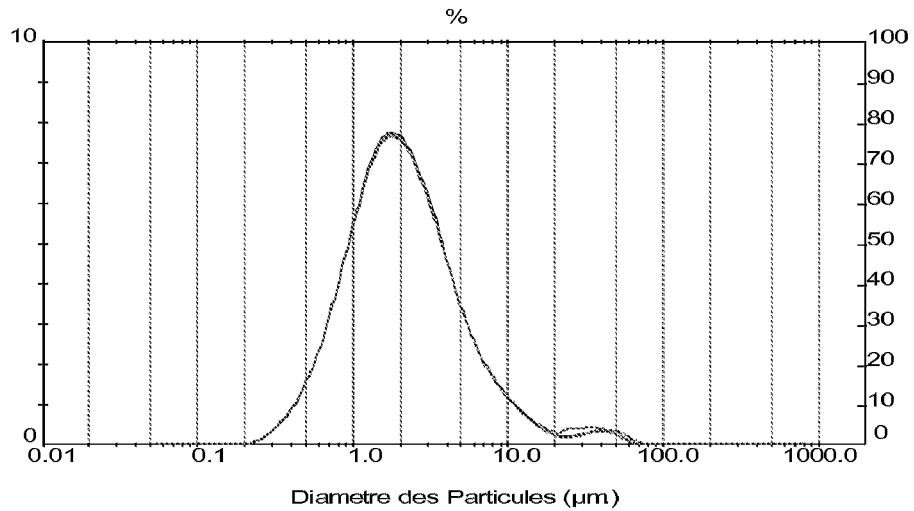
Figure 6:
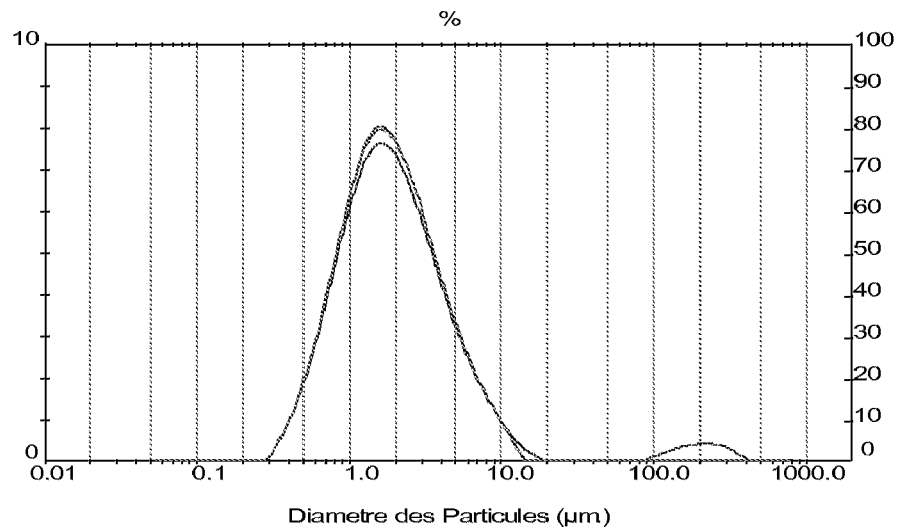

The size distribution of the fatty globules in the emulsion is illustrated in FIG. 3. The emulsion produced is fine and is on a nanometric scale, with an average diameter of 0.510 μm. The emulsion is stable for several days at ambient temperature. However, centrifugation at 4000 rpm for 20 minutes with an acceleration de 3500 g results in distinct phase separation. The emulsion therefore not stable.

It will also be noted that the pH of the emulsion obtained here is 7.5, whereas the pH of the emulsion of Example 1 is 5.85. This acidification appears to result from slight ionisation of the medium by the piezoelectric method, which stabilises the emulsion by means of the electrostatic bonds and therefore supplements the stabilisation achieved by controlling the size of the fatty globules (discontinuous phase).

Other Examples

Other emulsions were prepared under the conditions of Example 1 from rapeseed, olive and sunflower oils, without any emulsifier or surfactant (emulsion numbers 2 to 4). One emulsion was also prepared with added emulsifier (emulsion 5). The properties of these emulsions are summarised in the table below, which makes reference to the figure illustrating the size distribution of the discontinuous phase for each emulsion.

Emulsion 2 (rapeseed oil) exhibits a unimodal distribution of the fatty globules with a higher average diameter than previously (12.5 μm), but the system is nevertheless stable for several weeks.

| Ref. | Initial mixture (% wt./wt.) | Average diameter of the fatty globules of the emulsion | FIG. |
|---|---|---|---|
| 2 | Evian water + 5% rapeseed oil | 12.5 μm | 4 |
| 3 | Evian water + 5% olive oil | 3.7 μm | 5 |
| 4 | Evian water + 5% sunflower oil | 2.5 μm | 6 |
| 5 | Evian water + 8% sunflower oil + 0.05% Tween 80 | Complex distribution | 7 |

Emulsions 3 and 4 (olive and sunflower oils) exhibit a unimodal distribution of small fatty globules, with an average diameter of 3.7 and 2.5 μm respectively.

These emulsions do not undergo any phase separation when subjected to centrifugation under the conditions of Example 1.

These tests therefore confirm use of the present method for preparing fine, stable emulsions from food oils, without the addition of emulsifier, surfactant or other conventional stabiliser.

It will also be noted that the addition of Tween 80 in Example 5, a commonly used emulsifier known for its excellent capacity for stabilising emulsions, disrupts the particle size distribution of the discontinuous phase. It is here added to the mixture beforehand, that is to say before implementation of the high-frequency waves, as in the case of the production of an ordinary emulsion by stirring.

Figure 7:
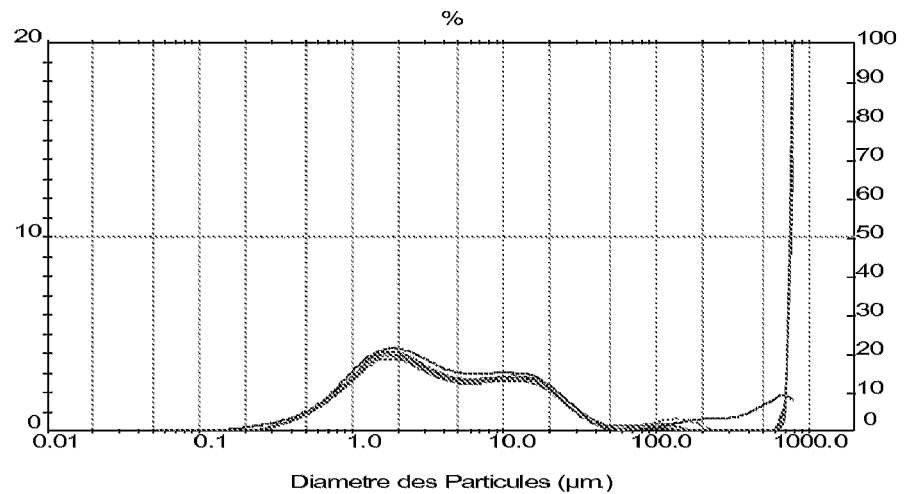

As can be seen in FIG. 7, three different populations of fatty globules have appeared. The first has an average diameter of the order of 2 μm, equivalent to that which had been analysed in the absence of emulsifier but a 2nd population centred around 10 μm makes its appearance, followed by a 3rd population composed of coarse agglomerates of a diameter larger than 1 mm (totally unstable very large fatty globules).

It would appear that the addition of emulsifier has a very negative effect on the fineness and homogeneity of the emulsion.

The invention claimed is:

1. A method of preparing a stable oil-in-water emulsion comprising combining a lipid or lipophilic phase with an aqueous phase, and exposing the mixture to vibratory energy in a closed receptacle by application of one or more transducers, wherein said one or more transducers operate only in a frequency range of between 900 kHz and 3 MHz.

2. The method according to claim 1, wherein the vibratory treatment is applied under substantially cavitation-free conditions.

3. The method according to claim 1, wherein the transducer operates at a frequency of less than 1,500 kHz.

4. The method according to claim 1, wherein the transducer operates at a frequency greater than 1 MHz.

5. The method according to claim 1, wherein the mixture, or emulsion, contains no added emulsifier.

6. The method according to claim 1, wherein the transducer is of the piezoelectric type.

7. The method according to claim 1, wherein the vibratory energy is applied to the mixture in the lower part of the closed receptacle containing the mixture.

8. The method according to claim 1, wherein the lipid phase constitutes no more than 40% of the total weight.

9. The method according to claim 1, wherein the mixture is kept within a predetermined temperature range.

10. The method according to claim 1, wherein the vibratory treatment is continued until the lipid phase is completely dispersed, the final desired lipid phase concentration is obtained or the final desired particle size is obtained.

11. The method according to claim 1, wherein the vibratory treatment is continued until a micrometric particle size is obtained.

12. The method according to claim 1, wherein the emulsion obtained is stable for several weeks to several months at ambient temperature.

13. The method according to claim 1 wherein the lipid phase constitutes no more than 30% of the total weight.

14. The method according to claim 1 wherein the lipid phase constitutes no more than 20% of the total weight.

15. The method according to claim 9 wherein the predetermined temperature range is between 20 and 30° C.

16. The method according to claim 10 wherein the vibratory treatment is continued until a discontinuous phase is obtained which has particles of an average diameter of less than 50 μm.

17. The method according to claim 10 wherein the vibratory treatment is continued until a discontinuous phase is obtained which has particles of an average diameter of less than 20 μm.

18. The method according to claim 1, wherein the vibratory treatment is continued until a nanometric particle size is obtained.

\* \* \* \* \*